United States Patent [19]

Dordick et al.

[11] Patent Number: 5,270,421
[45] Date of Patent: Dec. 14, 1993

[54] SUGAR-BASED POLYMERS

[75] Inventors: Jonathan S. Dordick; David G. Rethwisch, both of Iowa City; Damodar R. Patil, Coralville, all of Iowa

[73] Assignee: University of Iowa Research Foundation, Iowa City, Iowa

[21] Appl. No.: 918,926

[22] Filed: Jul. 22, 1992

Related U.S. Application Data

[63] Continuation of Ser. No. 521,076, May 8, 1990, abandoned.

[51] Int. Cl.$^5$ .................. C08G 63/00; C12P 19/04; C07H 13/02
[52] U.S. Cl. .................................... 527/311; 435/100; 435/101; 527/300; 536/115; 536/119
[58] Field of Search ............... 536/119, 115; 527/300, 527/311, 314; 435/100, 101

[56] References Cited

U.S. PATENT DOCUMENTS

| 3,225,012 | 12/1965 | Black et al. ............... 536/122 |
| 3,261,814 | 7/1966 | Friedman .................. 536/120 |
| 3,265,641 | 8/1966 | Wismer et al. ............. 536/124 |
| 3,400,107 | 9/1968 | Black et al. ............... 536/124 |
| 3,483,083 | 12/1969 | Elson et al. ............... 435/142 |
| 4,797,481 | 1/1989 | Garlisi et al. ............. 536/18.2 |
| 4,877,871 | 10/1989 | Klemann et al. ............ 536/124 |
| 4,952,687 | 8/1990 | Bodor et al. .............. 536/119 |
| 5,006,648 | 4/1991 | Van der Plank et al. ...... 536/119 |
| 5,024,942 | 6/1991 | Shimizu et al. ............ 435/134 |
| 5,128,248 | 7/1992 | Dordick et al. . |

FOREIGN PATENT DOCUMENTS 148058 5/1981 Fed. Rep. of Germany .

OTHER PUBLICATIONS

Guettes, Bernd et al., Chemical Abstracts, vol. 95(2), 1981, #188078v.
Ebert et al., Chemical Abstracts, vol. 67(21), 1967, #100362w.
News Release Dated Feb. 3, 1989 from The University of Iowa.
News Release Dated Apr. 26, 1989 from The University of Iowa.
"The Preparation of 4,6-Dichloro-4,6-Dideoxy-6O-D-Galactopyranosyl 6-Chloro-6-Deoxy-β-D-Fructofuranoside and the Conversion of Chlorinated Derivatives Into Anhydrides", Leslie Hough, Shashi P. Phadnis, and Edward Tarelli, Carbohydrate Research, 44 (1975) 37-44.
"C-Nuclear Magnetic Resonance (NMR) Spectra of O-Acylglucoses. Additivity of Shift Parameters and Its Application to Structure Elucidations", Kimihiro Yoshimoto, Yoshitaka Itatani, and Yoshisuke Tsuda, Chem. Pharm. Bull., 28(7) 2065-2076 (1980).
"Selective tetratosylation of sucrose: isolation of the 2,6,1',6'-tetrasulphonate", John M. Ballard, Leslie Hough, Shashi P. Phadnis, and Anthony C. Richardson, Carbohydrate Research, 83 (1980) 138-141.
"The Selective Removal of Protecting Groups in Carbohydrate Chemistry", Alan H. Haines, Academic Press, Inc., 1981.
"Chemistry and New Uses of Sucrose: How Important?", Riaz Khan, Pure & Appl. Chem., vol. 56, No. 7, pp. 833-844, 1984.
"Ester Synthesis in Organic Solvent Catalyzed by Lipases Immobilized on Hydrophilic Supports", C. Marlot, G. Langrand, C. Triantaphylides and J. Baratti, Biotechnology Letters, vol. 7, No. 9, 647-650 (1985).

(List continued on next page.)

Primary Examiner—Herbert J. Lilling
Attorney, Agent, or Firm—Willian Brinks Olds Hofer Gilson & Lione

[57] ABSTRACT

A method of making a novel sugar-based polymer is disclosed. A sugar and an organic acid derivative having at least two carboxylate functionalities are mixed in a substantially non-aqueous organic solvent with a hydrolytic enzyme and, thereafter, the resulting mixture is agitated for a time sufficient to allow for the polymerization of the sugar. The resulting sugar-based polymer has sugar incorporated in the polymer backbone.

12 Claims, No Drawings

OTHER PUBLICATIONS

"Enzyme-catalyzed processes in organic solvents", Aleksey Zaks and Alexander M. Klibanov, *Proc. Natl. Acad. Sci. USA*, vol. 82, pp. 3192-3196, May 1985.

"Facile Enzymatic Preparation of Monoacylated Sugars in Pyridine", Michel Therisod and Alexander M. Klibanov, *J. Am. Chem. Soc.*, vol. 108, No. 18, pp. 5638-5640, 1986.

"Enzymes that work in organic solvents", Alexander M. Klibanov, *CHEMTECH*, Jun. 1986.

"Lipase-Catalyzed Ester Exchange Reactions in Organic Media With Controlled Humidity", H. L. Goderis, G. Ampe, M. P. Feyten, B. L. Fouwe, W. M. Guffens, S. M. Van Cauwenbergh and P. P. Tobback, *Biotechnology and Bioengineering*, vol. XXX, pp. 258-266 (1987).

"Quantitative Analyses of Biochemical Kinetic Resolution of Enantiomers. 2. Enzyme-Catalyzed Esterifications in Water-Organic Solvent Biphasic Systems", Ching-Shih Chen, Shih-Hsiung Wu, Gary Girdaukas, and Charles J. Sih, *J. Am. Chem. Soc.* 1987, 109, 2812-2817.

"Stereoselective Oligomerizations Catalyzed by Lipases In Organic Solvents", Alexey L. Margolin, Jean-Yves Crenne, and Alexander M. Klibanov, *Tetrahedron Letters*, vol. 28, No. 15, pp. 1607-1610, 1987.

"Regioselective Acylation of Secondary Hydroxyl Groups in Sugars Catalyzed by Lipases in Organic Solvents", Michel Therisod and Alexander M. Klibanov, *J. Am. Chem. Soc.*, vol. 109, No. 13, pp. 3977-3981, 1987.

"Protease-Catalyzed Regioselective Esterification of Sugars and Related Compounds in Anhydrous Dimethylformamide", Sergio Riva, Joel Chopineau, A. P. G. Kieboom, and Alexander M. Klibanov, *J. Am. Chem. Soc.*, vol. 110, No. 2, pp. 584-589, 1988.

"Enzymatic Synthesis of Macrocyclic Lactones", Guo Zhi-Wei and Charles J. Sih, *J. Am. Chem. Soc.*, vol. 110, No. 6, pp. 1999-2001, 1988.

"Lipase-Catalyzed Irreversible Transesterifications Using Enol Esters as Acylating Reagents: Preparative Enantio- and Regioselective Syntheses of Alcohols, Glycerol Derivatives, Sugars, and Organometallics", Yi-Fong Wang, James J. Lalonde, Milagros Momongan, David E. Bergbreiter, and Chi-Huey Wong, *J. Am. Chem. Soc.*, vol. 110, No. 21, pp. 7200-7205, 1988.

"Carbonates in Water-Restriced Environments", Daniel A. Abramowicz and Charles R. Keese, *Biotechnology and Bioengineering*, vol. 33, pp. 149-156 (1989).

"Biocatalytic Synthesis of Polymers. Synthesis of an Optically Active, Epoxy-Substituted Polyester by Lipase-Catalyzed Polymerization", J. Shield Wallace and Cary J. Morrow, *Journal of Polymer Science: Part A: Polymer Chemistry*, vol. 27, 2553-2567 (1989).

"Enzymatic catalysis in monophasic organic solvents", Jonathan S. Dordick, *Enzyme Microb. Technol.*, 1989, vol. 11, Apr. 1989.

"Enzymatic catalysis in anhydrous organic solvents", Alexander M. Klibanov, *Trends in Biochemical Sciences*-Apr. 1989, vol. 14, No. 4.

"Enzymatic Synthesis of Various 1'-0-Sucrose and 1-0-Fructose Esters", Giacomo Carrea, Sergio Riva and Francesco Secundo, *Chem. Soc. Perkin Trans I*, 1989.

"Asymmetric Transformations Catalyzed by Enzymes in Organic Solvents", Alexander M. Klibanov, *Acc. Chem. Res.*, vol. 23, No. 4, pp. 23, 114-120, 1990.

SUGAR-BASED POLYMERS

This application is a continuation of application Ser. No. 07/521,076, filed May 8, 1990 and now abandoned.

BACKGROUND OF THE INVENTION

Americans create billions of pounds of plastic waste per year. A substantial portion of this plastic waste is discarded packaging materials and water-absorbent materials such as disposable diapers and hygienic products. Unfortunately, this plastic waste is substantially non-biodegradable; in fact, it takes approximately 450 years to degrade polyethylene, a major constituent of plastic waste. Accordingly environmentally unsound and potentially hazardous methods of disposing this waste must be utilized, as for example, by landfill or incineration. Furthermore, non-biodegradable plastic is often used in garbage bags which, in addition to creating a waste problem in of themselves, are impermeable to most bacterial agents thereby preventing microbial degradation of the contents within and, thus compounding the problem of waste disposal. These problems have lead to legislation in at least 12 states requiring certain products to be made of "degradable" plastic. Accordingly, health and environmental as well as legal concerns have recently increased interest in the development of biodegradable plastics.

Prior to the present invention, the major approach to imparting biodegradability to polymers such as polyethylene has been to make physical mixtures of the polymer with modified corn starch. The corn starch degrades leaving behind a porous polyethylene matrix which, in theory, due to the increased exposed surface area, is more prone to both chemical and microbial attack. However, the porous polyethylene remains fairly stable and is not easily biodegraded. Furthermore, chemical oxidants, added to the polyethylene and cornstarch formulation to increase the rate of degradation of the porous polyethylene matrix, could in and of themselves be potentially environmentally hazardous.

Sugar-containing polymers are not entirely new. For example, sucrose has been grafted onto poly(vinyl alcohol) via chemical etherification to produce "polysugars." These polymers have been proposed as non-caloric sweeteners. Similarly, sucrose-containing polymers, as for example, polyacrylic-sucrose graft polymers have been prepared for use as biodegradable body implants. These sucrose graft polymers can be manufactured by the chemical esterification of sucrose with large polymers. Unfortunately, these sucrose derivatives have a number of undesirable properties. For example, in these sucrose-containing polymers the sucrose is either grafted onto the polymer backbone or the polymer attaches to the sucrose molecule via an ester linkage, as opposed to the actual incorporation of the sucrose into the polymer backbone. Thus, the biodegradability of the sucrose does not necessarily guarantee biodegradability of the polymer backbone.

Proctor and Gamble. Inc. has produced the so-called "sucrose polyesters" for use as fat substitutes. However, these esters are not in fact polymeric materials. Rather, these "sucrose polyesters" are sucrose molecules with high degrees of substitution with fatty acid esters. Although displaying some degree of biodegradability, it has been determined that substitution of more than five oleic acid molecules per sucrose decreases the biodegradability of the sucrose polyester. To limit the extent of substitution on the sucrose molecule, expensive and time consuming chemical blocking techniques must be used. Additionally, unless all eight hydroxyl groups of sucrose are esterified, various isomers of sucrose pehta and hexa esters are produced. Each isomer has different properties that leads to different extents of biodegradability.

Prior to the discovery of the present invention, it was difficult to manufacture di-substituted sugars necessary for the synthesis of sugar-based polymers due to the poor selectivity of chemical synthesis. The randomly substituted sugar molecules which are the product of chemical synthesis are highly undesirable for use in the synthesis of sugar-based polymers, as the resulting polymers have a large, brittle network. Such polymers are undesirable for use in most commercial products.

Methods are available to increase the regioselectivity of chemical synthesis. These methods. however, invariably involve expensive and tedious blocking and deblocking steps. For example, sucrose contains three primary and five secondary hydroxyl groups. It is possible to chemically recognize primary groups solely via etherification with a bulky tertiary alkyl chloride such as trityl chloride. The size of the trityl group prevents any reaction at the secondary positions. This route has been used for the synthesis of sucrose-based sweeteners, yet has not been shown to be economically viable for large scale polymer synthesis.

Another limitation associated with chemical synthetic routes is the lack of control over the degree of substitution. In a typical chemical synthesis, mixtures of mono-, di-, tri-, and oligo-substituted sugar derivatives are formed. This variation and heavy degree of substitution severely impedes the synthesis of sugarbased polymers.

Clearly, if a method of acylating sugar molecules at consistent sites, as well as a method of controlling the degree of acylation were available then sugar molecules could be regioselectively acylated with an acid derivative having at least two carboxyl groups. The free carboxyl group of the resulting sugar ester could then react with a free hydroxyl group on another sugar ester to form a polymer having repeating sugar units in the polymer backbone. By limiting the degree of substitution on the sugar molecules, a polymer could be made having sugar molecules esterically bound with fatty acid linkages that could be utilized in various commercial products. Furthermore, by limiting the degree of substitution on the sugar molecules, it is contemplated that the undisturbed hydroxyl groups on the sugar molecules will cause the resulting sugar-based polymer to be water absorbent.

SUMMARY OF THE INVENTION

It has been discovered that biological acylation of sugar molecules overcomes the previously discussed shortcomings associated with chemical acylation of sugar. It has been discovered that enzymes are capable of di-substituting organic acid derivatives at very specific locations on sugar molecules by diacylating the sugar molecules with organic acid derivatives having at least two carboxyl functionalities, the resulting sugar esters can be polymerized to provide a sugar-based polymer. Therefore, in accordance with the present invention, a method of manufacturing a sugarbased polymer is provided.

The present invention further provides a novel sugar-based polymer wherein the sugar is incorporated into the polymer backbone itself. Without being restricted thereto, it is theorized that the sugar-based polymer will be biodegradable in that decomposition of the sugar molecules of the polymer backbone will result in decomposition of the polymer itself.

Many commercial products are comprised of polymers. Therefore, it is contemplated that such products can be manufactured using the sugar-based polymers of the present invention. Specifically, the present invention discloses sugar-based polymers which, in theory, are biodegradable. By employing the sugarbased polymers of the present invention in the manufacture of various commercial products it is contemplated that biodegradability can be imparted to such products.

In accordance with the present invention, a novel polymer is provided which incorporates an abundantly available and recyclable resource, sugar. Thus, for example, plastic products made with the sugarbased polymers of the present invention will be based, in large part, on a renewable resource. Whereas, polyethylene, the major component of most traditional plastics, is based on the more expensive and essentially non-renewable resource, petroleum.

In general, the present invention is directed to a method of making sugar-based polymers. In particular, a sugar and an organic acid derivative having at least two carboxyl functionalities are provided. The amount of sugar and organic acid derivative provided will be such that the molar ratio of reacting carboxyl groups on the organic acid derivative to reacting hydroxyl groups on the sugar is about 1:1. An amount of a hydrolytic enzyme is further provided. The hydrolytic enzyme should be capable of regioselectively di-acylating the sugar molecules with the organic acid derivative. Finally, a substantially non-aqueous organic solvent is provided. The organic solvent must be capable of solubilizing the sugar. The organic solvent, however, must not adversely affect the catalytic activity of the hydrolytic enzyme. Additionally, the organic solvent should not hydrolyze the acylated sugars. The sugar, organic acid derivative and hydrolytic enzyme are mixed in the organic solvent. The resulting mixture is then agitated for a period of time sufficient to allow for the polymerization of the sugar.

In another aspect of the present invention, a method of making an enzyme-acid derivative intermediate useful in the synthesis of sugar-based polymers is provided. According to this method, a substantially non-aqueous organic solvent is provided, in which, the hydrolytic enzyme is catalytically active. In the substantially non-aqueous organic solvent, a hydrolytic enzyme is mixed with an organic acid derivative having at least two carboxyl functionalities.

In yet another aspect of the present invention, an enzyme-acid derivative intermediate useful in the synthesis of sugar-based polymers is provided. The enzyme-acid derivative intermediate is of the general formula:

$$E-A$$

wherein A comprises an organic acid derivative having at least two carboxyl functionalities, and E comprises a hydrolytic enzyme.

In another aspect of the present invention, an enzyme-organic acid derivative-sugar intermediate useful in the synthesis of sugar-based polymers is provided. The enzyme-organic acid derivative-sugar intermediate is of the following general formula:

$$E-A-S$$

Wherein S is a sugar selected from the group consisting of mono-, di-, tri- and oligosaccharides: A comprises an organic acid derivative having at least two carboxyl functionalities; and E comprises a hydrolytic enzyme. In another aspect of the present invention a sugar-based polymer is provided. The sugar-based polymer is of the general formula:

$$(S-A)_n$$

wherein S is selected from the group consisting of a mono-, di-, tri- and oligosaccharides: A comprises an organic acid derivative having at least two carboxyl functionalities; and n is greater than or equal to 2.

DETAILED DESCRIPTION OF THE PRESENTLY PREFERRED EMBODIMENTS

In accordance with the present invention, the enzyme catalyzed regioselective acylation of sugar can be advantageously employed in the synthesis of sugar-based polymers. Specifically, sugar molecules are regioselectively di-acylated with an organic acid derivative having at least two carboxyl functionalities via the catalytic activity of a hydrolytic enzyme. Once acylated, selective ester linkages between the acid acyl groups of the sugar molecules can be obtained resulting in a sugar-fatty acid polymer. It is contemplated that the aforedescribed sugar-based polymer will be highly water-absorbent, due to the large number of free hydroxyl groups left underivatized on the sugar monomer by the selective enzymatic treatment. In addition, it is contemplated that the resulting sugar-based polymer will be highly biodegradable, as both aerobic and anaerobic microorganisms should have little difficulty breaking the polymer's ester bonds and metabolizing both its sugar and fatty acid constituents. Furthermore the sugar-based polymer incorporates an abundantly available and recyclable resource, sugar. These sugar-based polymers may find significant use as diaper liners, packing materials, drug delivery polymers, as well as in a variety of other commercial products.

The present invention contemplates that the sugar-based polymers of the present invention will be manufactured pursuant to enzyme catalyzed polymerization. Enzyme catalyzed polymerization offers several advantages over chemical sugar-polyester synthesis. The enzymes are capable of leaving undisturbed labile functionalities that might otherwise be destroyed in conventional chemical processing. Furthermore the ability of enzymes to regioselectively acylate the sugar molecules, as well as their ability to limit the degree of acylation, enables the synthesis of sugar-based polymers with regular size and backbone structures.

Enzymes are highly selective biological catalysts that typically operate under mild reaction conditions (e.g., ambient temperatures and pressures, neutral solutions, etc.). These properties make enzymes particularly attractive in the manufacture of the sugar-based polymers of the present invention. In particular, the present invention contemplates the utilization of hydrolytic enzymes. Hydrolytic enzymes comprise lipases, esterases proteases, and carbohydrases. In an aqueous environment, hydrolytic enzymes are capable of catalyzing both hydrolysis and ester formation according to the following general formula:

In aqueous systems however the large concentration of water (ca. 55 M), results in a low equilibrium yield of ester. Thus, although lipases and esterases have been employed to synthesize sugar esters of fatty acids in aqueous solutions, low yields of the sugar esters are achieved due to the hydrolysis of the product in the aqueous solution.

However, the use of enzymes in substantially non-aqueous organic solvents dramatically increases the yield of sugar esters. Thus, the present invention contemplates taking advantage of organic solvents to catalyze the synthesis of sugar esters and the subsequent polymerization of these sugar esters. Unfortunately, however, sugars are soluble in only a very few organic solvents. Additionally, most hydrolytic enzymes lose their catalytic activity in the few organic solvents capable of solubilizing sugars.

According to the present invention, various organic solvents are screened for their ability to solubilize sugar, as well as their ability to leave unaffected the catalytic activity of various hydrolytic enzymes. Once having determined the compatibility of various sugars, hydrolytic catalysts and organic solvents, a sugar-based polymer may be made.

In accordance with one embodiment of the present invention, a sugar is provided. The present invention contemplates the utilization of mono-, di-, tri- and oligosaccharides as the sugar. Examples of suitable sugars are glucose, mannose and fructose (monosaccharides): sucrose, lactose, maltose, trehalose (disaccharides): and raffinose (a trisaccharide). The presently preferred sugars for use in the present invention are sucrose and fructose. The most preferred sugar, however, is sucrose.

In addition to sugar, an amount of an organic acid derivative having at least two carboxyl functionalities is provided. Any organic acid derivative having at least two carboxyl functionalities is contemplated for use in the present invention. Preferably, the organic acid derivative will be of the general formula:

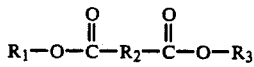

wherein $R_1$ and $R_3$ comprise groups capable of leaving the acid and $R_2$ is any moiety which will not interfere with the acylation of the sugar with the organic acid derivative and subsequent polymerization of the resulting sugar esters. For example. $R_2$ could be selected from the group consisting of alkanes, branched alkanes, alkenes, substituted alkenes, and aromatic moieties. The only requirement with respect to $R_2$ is that it not contain a reacting functionality (as, for example, a hydroxyl or an amine) which would interfere with the acylation, and subsequent polymerization, of the sugar, preferably, $R_1$ and $R_3$ are leaving groups which are poorer nucleophiles than the sugar. Most preferably, $R_1$ and $R_2$ are selected from the group consisting of: mono-, di-, and trifluoro ethanols: mono-, di-, and tricloroethanols: and enol esters. Presently, the most preferred organic acid derivative contemplated for use in the present invention is bis(2.2.2-trifluoroethyl)adipate.

The choice of the organic acid derivative may be dictated by various consideration. As provided above, the organic acid derivative will preferably have good leaving groups which are also poorer nucleophiles than the sugar (i.e. $R_1$ and $R_3$ in the above equation). This is important because, as presently understood, the sugar molecules react with an enzyme-organic acid derivative intermediate via a nucleophilic mechanism. Thus, where $R_1$ and $R_3$ are poor nucleophiles, there will be little competition between these groups and the sugar molecules, thus yielding a higher amount of sugar esters and, ultimately, a sugar-based polymer having a relatively higher molecular weight than if $R_1$ and $R_3$ were relatively good nucleophiles. Also, the properties desired of the final sugar-based polymer should be considered when selecting the organic acid derivative. As the $R_2$ group of the organic acid derivative will ultimately be incorporated into the backbone of the sugar-based polymer, the properties of the sugar-based polymer will be heavily dependent on the character of this $R_2$ group. Longer $R_2$ groups will result in longer hydrocarbon links which will increase the flexibility of the polymer backbone and decrease the hydrophilicity of the polymer. Conversely. shorter hydrocarbon links will increase the hydrophilicity and rigidity of the resulting sugar-based polymer.

In some applications it may be desirable to cross-link the sugar-based polymers. For example, where shorter hydrocarbon chains are employed, the polymer will be hydrophilic and potentially water soluble. Light cross-linking would result in a polymer which could swell and absorb water: the polymer remaining insoluble. This will be particularly important with lower molecular weight polymers. One approach of providing cross-linking capability to the sugar-based polymer is via the use of an unsaturated fatty acid at the $R_2$ portion of the organic acid derivative thereby resulting in the incorporation of unsaturated fatty acid chains in the sugar-based polymer. Heating or irradiating the polymer would cause cross-linking to occur at the unsaturated bonds resulting in a thermosetting or photosetting sugar-based polymer. The polymers could also be cross-linked during the esterification process by adding higher functional acids such as tri- and tetracids to the initial reaction mixture. Each of the higher functionality acids acting as a cross-linking point.

In some cases, high crystallinity of the sugar-based polymer will be desired as, for example, where the polymer is contemplated for use as a thermoplastic material. However, for other uses (e.g., clear plastic packaging films) a non-crystalline polymer is preferred. Crystallinity can be enhanced by regularity in the polymer backbone and by increasing the high polarity of the polymer. This can be achieved by varying the nature of the $R_2$ group of the organic acid derivative. To decrease the crystallinity of the sugar-based polymer two approaches can be used. First to disrupt the regularity of the polymer (and, thus, decrease crystallinity) organic acid derivatives having two different linkage lengths (i.e. different $R_2$ groups) may be employed in a single synthesis of the sugar-based polymer. This should result in a random copolymer (i.e.. the two lengths should be randomly distributed in the polymer chain, thereby decreasing regularity). The second approach is to decrease the polarity of the sugar-based polymer by using longer, more hydrophobic $R_2$ groups in the organic acid derivative. As the polarity decreases the crystallinity may decrease.

As can be discerned from the preceding discussion, by varying the character of the $R_2$ group in the organic acid derivative, the properties of the resulting sugar-based polymer may be modified. The only practical limitation on the nature of the $R_2$ group is that the organic acid derivative should be soluble in the substantially non-aqueous organic solvent.

The sugar molecules must be acylated at two locations in order to synthesize the sugar-based polymers of the present invention. The ratio of reacting acid groups on the organic acid derivative to the reacting hydroxyl groups on the sugar should be about 1:1. Of course where a tri, tetra, or higher organic acid derivative are used as the acyl donor, the ratio of the organic acid derivative to sucrose will be adjusted according to the aforesaid ratio. The 1:1 ratio should not be substantially deviated from as subsequent polymerization of the sugar esters will most likely be adversely effected.

The present invention contemplates the use of enzymes to catalyze the regioselective di-acylation of the sugar molecules with the organic acid derivative and the subsequent polymerization of the resulting sugar esters. Hydrolytic enzymes are contemplated for use in the present invention. Hydrolytic enzymes include lipases, esterases, proteases, and carbohydrases. Unfortunately, many hydrolytic enzymes are catalytically inactive in the majority of organic solvents capable of solubilizing sugars to an appreciable degree. Several hydrolytic enzymes have been found to retain their catalytic activity, however, in either pyridine or dimethylformamide. Applicants have ascertained that the following hydrolytic enzymes are catalytically active in pyridine: Aminoacylase; Lipozyme, available from NOVO CHEMICAL; Fungal Amylase, available under the trade name "HT" from MILES KALI-CHEMIE: Bacterial protease. available under the trade name "Bioenzyme from GIST-BROCADES; Amylase from *B. Subtiles* available under the trade name Rapidase from GIST-BROCADES; Alkaline protease, available under the trade name "Proleather" from AMANO; Bacillus protease available under the trade name Protease N from AMANO: Lipase from *C. cylindracea*, available from SIGMA; Lipase from porcine pancreas, available from SIGMA; and Lipase from Penicillium Sp., available under the trade name Lipase G from AMANO. Additionally. Applicants have determined that subtilisin is catalytically active in dimethylformamide. Both highly purified or crude subtilisin are catalytically active: however, the substantially less expensive crude subtilisin is preferred. Although specific to the organic solvent, it should be noted that, as presently understood, the hydrolytic enzymes are non-specific to the organic acid derivative used in the synthesis of the sugar-based polymers of the present invention. Finally, the present invention contemplates the use of a substantially non-aqueous organic solvent capable of solubilizing sugar. Sugars are reasonably soluble in only a few, very hydrophilic organic solvents as, for example, pyridine, dimethylformamide, morpholine N-methylpyrolidone, and dimethylsulfoxide. Care should be taken, however, in selecting an appropriate organic solvent in that the organic solvent should be screened to assure that it does not significantly detract from the catalytic activity of the enzyme contemplated for use in the acylation and, ultimately, the polymerization of the resulting sugar-esters. Additionally, the organic solvent should not hydrolyze the sugar-ester products of the acylation of the sugar molecules with the organic acid derivative. Of the previously mentioned organic solvents, pyridine and dimethylformamide appear to have the least adverse affect on the catalytic activity of hydrolytic enzymes and, thus, are the preferred organic solvents for use in the present invention. The most preferred organic solvent for use in the present invention, however, is pyridine, as the majority of hydrolytic enzymes screened retain their catalytic activity in this solvent.

Where pyridine is the organic solvent, the presently preferred enzymes are alkaline protease. Bacterial protease, Bacillus protease, and aminoacylease. At present, the most preferred hydrolytic enzyme in pyridine is activated alkaline protease. By activated alkaline protease it is meant that the alkaline protease is activated by dissolving the enzyme in about 20 mmol sodium borate butter at a pH of about 9.5, and dialyzing the resulting mixture against added butter. Thereafter, the dialyzed protein is freeze dried. However, where dimethylformamide is the organic solvent selected, the presently preferred enzyme is subtilisin. The amount of hydrolytic enzyme provided to catalyze the regioselective acylation of the sugar molecules and their subsequent polymerization is not critical. By varying the amount of enzyme employed, however, the speed of the reaction can be affected. In general, increasing the amount of hydrolytic enzyme increases the speed of the acylation, and subsequent polymerization, of the sugar.

An amount of the sugar, organic acid derivative and hydrolytic enzyme are mixed in the substantially non-aqueous organic solvent. The amount of hydrolytic enzyme should be sufficient to initiate the regioselective diacylation of the sugar molecules with the organic acid derivative. The amount of the organic acid derivative and sugar in the aforesaid mixture should be such that the ratio of reacting carboxyl groups on the organic acid derivative to reacting hydroxyl groups on the sugar is at least about 1:1. As used herein, the phrases "reacting carboxyl groups" and "reacting hydroxyl groups" refers to the carboxyl groups on the acid derivative that react with the hydroxyl groups on the sugar molecules. Preferably, however, the ratio of reacting carboxyl groups on the organic acid derivative to reacting hydroxyl groups on the sugar is about 1:1.

The aforesaid ingredients may be mixed in the substantially non-aqueous solvent according to any method known by those skilled in the art. The preferred method, however, is as follows. The sugar and organic acid derivative are mixed with the substantially non-aqueous organic solvent. Thereafter, the hydrolytic enzyme is added to initiate the acylation of the sugar with the organic acid derivative and the polymerization of the resulting sugar esters.

Upon mixing, the resulting mixture is agitated for a period of time sufficient to allow for the polymerization of the sugar molecules. A suitable time period, for example, is about 8 to about 28 days. Once again any method of agitation known by those skilled in the art is contemplated by the present invention, as for example, magnetic stirring or overhead mechanical stirring. Once the sugar molecules have been allowed to polymerize, the hydrolytic enzyme may be filtered from the mixture. Any method of filtration known by those skilled in the art is suitable as, for example, using a Buchner funnel.

Finally, the substantially non-aqueous organic solvent is evaporated off the mixture leaving behind the sugar-based polymer of the present invention. All methods of evaporating off the organic solvent known by those skilled in the art are contemplated by the present invention, as for example, rotary evaporation.

Without being restricted thereto, it is presently theorized that the polymerization of the sugar molecules takes place according to the following mechanism. An organic acid derivative ("A" below) having at least two carboxylate functionalities is provided:

A

Preferably, the organic acid derivative will have the following general formula:

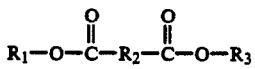

Wherein $R_1$ and $R_3$ are leaving groups capable of leaving the acid and $R_2$ is any moiety which will not interfere with the acylation, and subsequent polymerization, of the sugar. For example, $R_2$ can be selected from the group consisting of alkanes, branched alkanes, alkenes, substituted alkenes and aromatic moieties. Most preferably, $R_1$ and $R_3$ are selected from the group consisting of mono- di-, and trifluoroethanols; mono-. di-, and trichloroethanols; and enol esters.

Upon mixing the organic acid derivative and hydrolytic enzyme in a substantially non-aqueous organic solvent, in which the hydrolytic enzyme is catalytically active, it is theorized that the enzyme replaces a leaving group on the organic acid derivative yielding the following enzyme-organic acid derivative intermediate:

E—A

Wherein E is the hydrolytic enzyme and A comprises an organic acid derivative having at least two carboxyl functionalities.

Once this above-described enzyme-organic acid derivative intermediate is formed, the sugar molecules replace the enzyme on this intermediate via a nucleophilic mechanism. As a result, a sugar-organic acid derivative intermediate is formed having the following general formula:

S—A

Wherein S is a sugar selected from the group consisting of mono-, di-, tri- and oligosaccharides; and A comprises the above described organic acid derivative having at least two carboxylate functionalities.

The above described sugar-organic acid derivative intermediate then reacts with the hydrolytic enzyme. The hydrolytic enzyme replaces a leaving group on this intermediate to yield a sugar-organic acid derivative-enzyme intermediate of the following general formula:

S—A—E

Wherein S and A are as above, and E is a hydrolytic enzyme. Another sugar molecule then replaces E in the above formula via a nucleophilic mechanism, and, thus, by employing sugars that can be regioselectively acylated on at least two locations, a sugar-based polymer can be synthesized having the following formula:

$(S—A)_n$

Wherein S is selected from the group consisting of mono-, di-, tri- and oligosaccharides, A is an organic acid derivative having at least two carboxyl functionalities, and n is greater than or equal to 2.

It is to be understood that an equivalent of changes and modification of the above described embodiments are also contemplated by the present invention. The following examples are not to be construed as limitations upon the present invention, the scope of which is defined by the claims appended hereto, but are included merely as an illustration of various embodiments.

EXAMPLES

Example 1

In order to identify enzymes capable of catalyzing the synthesis of sucrose-based polymers, a variety of hydrolytic enzymes were screened for their ability to synthesize sucrose butyrate in pyridine. In this manner, simple esters of sucrose were obtained and structurally analyzed without the added complication of polymer formation. Trifluoroethylbutyrate was chosen as the butyrate donor. In all 15 enzymes were studied for sucrose-butyrate synthesis (Table 1). A typical reaction mixture contained 0.1 M sucrose dissolved in 2 mL anhydrous pyridine containing 0.6 M trifluoroethylbutyrate. The 6:1 molar ration of trifluoroethylbutyrate to sucrose was chosen to expedite the reaction. The reactions were initiated by the addition of 0.25 g/mL enzyme (0.015 g/mL in the case of "proleather". an alkaline protease obtained from Amano) and agitation at 250 rpm and 45° C. Sucrose disappearance was monitored by HPLC. As can be discerned from Table 1. the five most active enzymes were Alkaline Protease Bacterial Protease; Bacillus protease; Aminoacylase, and subtilisin.

Example 2

The five most catalytically active enzymes from Example 1 were subjected to a 25 mL reaction scale (same concentrations of reactants and enzyme in Example 1). After the time scale indicated in Table 2 the reactions were terminated and the solvent evaporated. The residual solids were chromatographed on silica gel (17:2:1; ethyl acetate: methanol:water) and the sucrose ester products separated. Clearly, as can be discerned from Table 2. the alkaline protease ("proleather") produced the highest ratio of sucrose dibutyrate to monobutyrate. The production of the sucrose dibutyrate is vital for the subsequent synthesis of the sucrose-based polymer of the present invention. $^{13}$-C-NMR analysis of the proleather mono- and diester products indicated that the sucrose is first acylated in the 1' position followed by acylation at the 6 position.

Example 3

As can be discerned from TABLES 1 and 2 of the fifteen enzymes considered, proleather was the ideal choice to carry out the synthesis of a sucrose-based polymer. In this example, bis(2,2,2-trifluoroethyl) adipate was selected as the organic acid derivative. Sucrose (0.1M) was dissolved in 25 mL anhydrous pyridine containing 0.1M bis(2.2.2-trifluoroethyl) adipate. The reaction was initiated by the addition of 0.015 g/mL activated proleather and the reaction magnetically stirred at 100 rpm and 45° C. under a slight nitrogen stream. The ratio of sucrose to the diacid derivative was purposely chosen to be equimolar as it was expected that two hydroxyls on sucrose would readily react with the two acid functionalities of the organic acid derivative. (Proleather did not catalyze the synthesis of sucrose tributyrates in the aforementioned experiment.)

The progress of the reaction was followed by gel permeation chromatography (gpc) HPLC. The reaction was terminated after 28 days (80% conversion of the sucrose). the enzyme removed by filtration, and the pyridine and bis(2,2,2-trifluoroethyl) adipate removed by rotary evaporation. The products of the reaction were completely water-soluble as well as having high solubilities in polar organic solvents including methanol, ethanol, pyridine, dimethylformamide, and dimethylsulfoxide. While the reaction was slow, gpc data showed the formation of higher molecular weight species as reaction time increased. Molecules with molecular weights in excess of 10.000 were produced. The average molecular weight was determined following dialysis of the product (through a 1000 dalton dialysis bag to remove unreacted sucrose and low molecular weight mono- and diester products). The dialyzed product was shown to have a weight average molecular weight of 2110 and a number average molecular weight of 1555 therefore giving a polydispersity of 1.36. The polyester showed selective linkages between the adipic acid functionalities and the 6 and 1' positions of the sucrose as determined by $^{13}$C-NMR. From the NMR data it is clear that a shift in the positions of the 6 and 1' carbons has occurred indicative of acylation at those positions. The resulting sucrose-based polymer has a decomposition temperature of about 150° C.

The abovedescribed synthesis of sucrose-based polymers has shown clearly that enzymes are capable of acting as highly selective polymerization catalysts in the manufacture of sugar-based polymers. It is to be understood that a variety of sugars, organic acid derivatives, organic solvents, and hydrolytic enzymes can be substituted for those specified above and mixed in similar proportions to make various sugar-based polymers. The preceding examples should in no way be construed as limiting the extent of the present invention the scope of which is defined by the following claims.

TABLE 1

| Screen of Enzymes for Sucrose-Butyrate Synthesis[a] | |
|---|---|
| Enzyme | Sucrose Conversion (120 h) |
| Control (no enzyme) | 0% |
| Lipase from As Spergillus Sp. | 0% |
| Aminoacylase | 70% |
| Lipozyme (Novo) | 8% |
| Fungal Amylase (HT from Rohm) | 34% |
| Bacterial protease (Bioenzyme) | 100% |
| Amylase from B. subtilis (Rapidase from Gist-Brocades) | 24% |
| Rhizopus Sp. Lipase | 0% |
| Alkaline protease (Amano-Proleather) | 96% |
| Bacillus protease | 65% |
| Lipase from Pseudomonas Sp. (Amano P) | 0% |
| Lipase from C. cylindracea (Sigma) | 7% |
| Lipase from porcine pancreas (Sigma) | 13% |
| Yeast Esterase (Sturge, Ltd.) | 0% |
| Crude subtilisin (Amano protease N) | 83% (in dimethylformamide) |
| Lipase from Penicillium Sp. | 24% |

TABLE 1-continued

| Screen of Enzymes for Sucrose-Butyrate Synthesis[a] | |
|---|---|
| Enzyme | Sucrose Conversion (120 h) |
| (Amano G) | |

[a]Conditions: Sucrose (0.1 M) dissolved in 2 Ml pyridine containing 0.6 M trifluoroethylbutyrate. Reaction initiated by addition of 0.25 g/Ml enzyme and shaken at 250 rpm at 45° C.

TABLE 2

| | Enzymatic Synthesis of Sucrose Butyrates[a] | | | |
|---|---|---|---|---|
| Enzyme | Total Conversion | Isolated Yield | 1'-Ester | 6.1'-Diester |
| Alkaline Protease (Proleather) | 99% (8 days) | 0.5 g (43%) | 0.12 g | 0.38 g |
| Bacterial Protease (Bioenzyme) | 100% (8 days) | 0.57 g (52%) | 0.30 g | 0.27 g |
| Bacillus Protease | 62% (21 days) | 0.39 g (37%) | 0.31 g | 0.08 g |
| Aminoacylase | 67% (23 days) | 0.54 g (49%) | 0.26 g | 0.28 g |
| Crude Subtilisin in DMF | 62% (25 days) | 0.91 g (84%) | 0.66 g | 0.25 g |

[a]Conditions: Sucrose (0.1 M) dissolved in 25 Ml pyridine (except with subtilisin) containing 0.25 g/Ml enzyme and 0.6 M trifluoroethylbutyrate, magnetically stirred at 150 rpm at 45° C.

We claim:

1. A composition of matter comprising sugar-based copolymer comprising a polymer backbone of sugar molecules esterically linked to organic acid derivatives, the polymer backbone having the formula:

wherein

S comprises sucrose linked at the C-6 and C-1' positions;

A comprises an organic acid derivatives having at least two carboxyl functionalities; and the copolymer having a weight average molecular weight of at least 2110.

2. The sugar-based polymer of claim 1 wherein the organic acid derivative

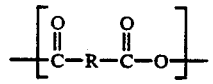

comprises adipate.

3. A sugar-based copolymer comprising a polymer backbone of sucrose molecules esterically linked to organic acid derivatives prepared by:

providing sucrose;

providing organic acid derivative having at least two carboxyl functionalities;

providing hydrolytic enzyme selected from the group consisting of aminoacylase, lipozyme, fungal amylase, bacterial protease, amylase from B. subtiles, alkaline protease, Bacillus protease, lipase from C. cylindracea, lipase for porcine pancrease, lipase from Penicillium Sp., subtilisin, and mixtures thereof;

providing a substantially non-aqueous organic solvent;

preparing a reaction mixture by mixing in the organic solvent an amount of the sucrose and an amount of the organic acid derivative such that the molar ratio of reacting carboxyl groups on the organic acid derivative to reacting hydroxyl groups on the sucrose is about 1:1, and an amount of the hydrolytic enzyme sufficient to catalyze the regioselective diacylation of the sucrose with the organic acid derivative;

agitating the reaction mixture for a period of time sufficient to allow for the formation of the sugar-based polymer; and isolating the resulting sugar-based polymer from t he reaction mixture.

4. The sugar-based polymer of claim 3 wherein the organic acid derivative is selected from the group consisting of vinyl diacetate, bis(2,2,2-trifluoroethyl) adipate, bis(2,2,2-trichloroethyl) adipate and mixtures thereof.

5. The sugar-based polymer of claim 3 wherein the organic solvent comprises dimethylformamide.

6. The sugar-based polymer of claim 5 wherein the hydrolytic enzyme comprises subtilisin.

7. The sugar-based polymer of claim 6 wherein the organic acid derivative is selected from the group consisting of vinyl diacetate, bis(2,2,2-trifluoroethyl) adipate, bis(2,2,2-trichloroethyl) adipate and mixtures thereof.

8. A composition of matter comprising a copolymer having a polymer backbone consisting essentially of sucrose molecules esterically linked at 6 and 1' positions by organic diacid derivatives and having a weight average molecular molecular weight of at least 2210.

9. The copolymer of claim 8 having a molecular weight of greater than about 10,000.

10. The copolymer of claim 1 having a molecular weight of greater than about 10,000.

11. A copolymer having a weight average molecular weight of at least 2110 and the structure:

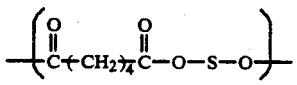

wherein S comprises sucrose esterically linked at the C-6 and C-1' positions.

12. The copolymer of claim 11 having a molecular weight greater than about 10,000.

* * * * *

UNITED STATES PATENT AND TRADEMARK OFFICE
CERTIFICATE OF CORRECTION

PATENT NO. : 5,270,421
DATED : December 14, 1993
INVENTOR(S) : Jonathan S. Dordick et al.

It is certified that error appears in the above-indentified patent and that said Letters Patent is hereby corrected as shown below:

Column 12, line 36:
In claim 1, line 9, delete "derivatives" and substitute --derivative--.

Column 12, line 42:
In claim 2, line 2, immediately after "derivative" and before "comprises" delete the chemical structure representation.

Column 14, line 7:
In claim 8, line 5, delete the second occurrence of "molecular".

Signed and Sealed this

Sixteenth Day of January, 1996

Attest:

BRUCE LEHMAN

Attesting Officer

Commissioner of Patents and Trademarks